(12) United States Patent
St Amant, III (10) Patent No.: US 9,995,659 B1
(45) Date of Patent: Jun. 12, 2018

(54) WET GAS LATERAL SAMPLING SYSTEM AND METHOD

(71) Applicant: Mayeaux Holding LLC, Gonzales, LA (US)

(72) Inventor: Valmond Joseph St Amant, III, St Amant, LA (US)

(73) Assignee: Mayeaux Holding LLC, Gonzales, LA (US)

( * ) Notice: Subject to any disclaimer, the term of this patent is extended or adjusted under 35 U.S.C. 154(b) by 300 days.

(21) Appl. No.: 14/214,225

(22) Filed: Mar. 14, 2014

Related U.S. Application Data (60) Provisional application No. 61/798,287, filed on Mar. 15, 2013.

(51) Int. Cl.
*G01N 1/22* (2006.01)

(52) U.S. Cl.
CPC .................... *G01N 1/2247* (2013.01)

(58) Field of Classification Search
CPC .. G01N 1/12; G01N 1/16; G01N 1/18; G01N 1/20; G01N 1/22; G01N 1/2247; G01N 2001/2285; G01N 2001/2291
See application file for complete search history.

(56) References Cited

U.S. PATENT DOCUMENTS

| | | | | |
|---|---|---|---|---|
| 3,080,760 A | * | 3/1963 | Piersma | G01N 1/08 73/863.31 |
| 4,537,071 A | * | 8/1985 | Waterman | B25B 27/143 73/866.5 |
| 4,625,570 A | * | 12/1986 | Witherspoon | G01N 1/20 73/863.81 |
| 4,790,198 A | * | 12/1988 | Awtry | G01N 1/08 73/864.64 |
| 5,154,087 A | * | 10/1992 | Wenshau | G01N 1/08 73/863.81 |
| 5,179,859 A | * | 1/1993 | Van Niekerk | G01N 1/08 73/864.64 |
| 5,237,878 A | * | 8/1993 | Hackenberg | G01N 1/14 73/861.34 |
| 5,440,941 A | * | 8/1995 | Kalidindi | G01N 1/08 73/864.64 |

(Continued)

OTHER PUBLICATIONS

A+Corporation LLC, Genie tm High Velocity Probe product sheet, 2003.

(Continued)

*Primary Examiner* — Natalie Huls
(74) *Attorney, Agent, or Firm* — Joseph T Regard, Ltd plc (57) ABSTRACT

A system for on-stream sampling of pressurized process gas such as natural gas or the like, said system optimized for use with pressurized process gas having liquid entrained therein, or otherwise referenced as "wet". In the preferred embodiment, the probe tip is situated laterally from one side of the inner pipe wall to the other so as to span the entire inner diameter (ID) of the pipe, the probe tip having formed along its outer surface sample collection slot along the length of said outer surface, providing a "linear sample" of the fluid flow of the entire breadth of the flow, providing an accurate sample of even disassociated flow with entrained liquid particles and flow. Embodiments for continuous sampling, batch mode, spot sampling are provided, as well as an anti-vibration feature.

24 Claims, 9 Drawing Sheets

(56) References Cited

U.S. PATENT DOCUMENTS

| | | | |
|---|---|---|---|
| 5,538,344 A | | 7/1996 | Dybdahl |
| 5,834,657 A | * | 11/1998 | Clawson .............. G01N 1/2035 73/863.51 |
| 6,869,800 B2 | * | 3/2005 | Torgerson .............. B01J 8/0035 422/62 |
| 7,958,794 B2 | * | 6/2011 | Sahibzada ............ G01N 1/2247 73/23.2 |
| 9,200,986 B1 | * | 12/2015 | Mayeaux .................. G01N 1/10 |
| 9,257,027 B2 | * | 2/2016 | Williamson ........... G08B 17/10 |
| 2011/0036445 A1 | * | 2/2011 | Hall ..................... G01N 1/2273 138/96 R |
| 2012/0033219 A1 | * | 2/2012 | Hokamura ............. G01N 21/15 356/438 |
| 2013/0220036 A1 | * | 8/2013 | Faust ...................... G01N 1/20 73/863.41 |

OTHER PUBLICATIONS

Matheson Gas, "The BTU Accuracy Connection to Profitability . . . " 2 page brochure, 2010.

\* cited by examiner

WET GAS LATERAL SAMPLING SYSTEM AND METHOD

DOMESTIC PRIORITY DATA CLAIMED BY APPLICANT

The present application claims the benefit of U.S. Provisional Patent Application Ser. No. 61/798,287, filed Mar. 15, 2013, listing as inventor Valmond Joseph T. Amant, III, entitled "Wet Gas Lateral Sampling System and Method".

FIELD OF THE INVENTION

The present invention relates to sampling of pressurized process gas, and in particular to a system for on-stream sampling of pressurized process gas such as natural gas or the like, said pressurized process gas having liquid entrained therein, or otherwise referenced as "wet". The preferred embodiment of the present invention contemplates a system for obtaining an accurate sample of said wet process gas.

BACKGROUND OF THE INVENTION

Natural gas is bought and sold based on its heating value. It is the BTU content that determines the monetary value of a given volume of natural gas. This BTU value is generally expressed in decatherms (one million BTU). In the determination of total heat value of a given volume of gas, a sample of the gas is analyzed and from the composition and its heat value per unit volume is calculated. This value is generally expressed in BTU/cu ft. The typical range of transmission quality gas ranges between 1000 and 1100 BTU/cu ft. Production gas and new found Shale Gas can have heating values exceeding 1500 BTU/cu ft.

There has been a long standing controversy between gas producers and gas transporters regarding entrained liquid typically present in most high BTU/cu ft gas (rich or wet gas). Transporter tariffs require essentially liquid-free gas. Hydrocarbon liquid in the gas being transported causes operational and safety problems. The practice is to separate the liquid before entering a transport (pipe) line.

The API 14.1 standards (Manual of Petroleum Measurement Standards, 2006) scope does not include "wet gas" (a term referenced by the Natural Gas industry as a gas that is at its hydrocarbon dew point temperature and/or contains entrained liquid), nor does the GPA 2166 standard (Obtaining Natural Gas Samples for Analysis by Gas Chromatography, 2005). In summary, there is no known standard which defines how to obtain a "representative sample" of a natural gas supply having entrained hydrocarbon in any form.

The liquid hydrocarbon (HC) content of a Natural gas is comprised mainly of the heavier (higher molecular weights such as propane, ethane and octane) components. Therefore its heating value is high, and of great monetary value. This is the reason that producers wish to have the liquid HC represented in the sample composition utilized for computing the BTU/cu ft content.

The API 14.1 standard, Appendix B section B-3 Multiphase Flow states that:

"Sampling of multiphase flow is outside the scope of this standard. Sampling of multiphase (gas and liquid) mixtures is not recommended and should be avoided if at all possible. In the multiphase flow, the ideal system would mix the gas and liquid flows uniformly and collect a sample of the true mixture flowing in the line by using a properly designed sample probe and an isokinetic sampling system. Current technology of natural gas sampling is not sufficiently advanced to accomplish this with reasonable accuracy. When sampling a multiphase liquid-gas flow, the recommended procedure is to eliminate the liquid from the sample. The liquid product that flows through the line should be determined by another method. The liquid fraction of the multiphase flow may contain water and hydrocarbons. The hydrocarbons can contribute significantly to the energy (measured in British thermal units) content of the gas and their presence in the gas line must not be overlooked."

The GPA 2166 standard's scope states that the standard is not designed for sampling Natural gas that is at or below its HC dew point temperature. Within the body of this standard several references are made to avoiding liquid entrainment and condensation due to its impact on sample composition and the calculated heat value.

The API 14.1 and GPA 2166 are the primary standards utilized by most Gas companies to guide their sampling methods. Both state that they are not intended for obtaining a Natural gas sample representing a combined gas and liquid.

There have been many attempts to achieve the representative sampling of Natural gas/HC liquid mixture. Most methods use a dynamic flow isokinetic technique. In an ideal world, gas having liquid droplets suspended would be homogenized (ideally mixed) and would then be directed into the entrance port of a sample probe (isokinetic probe), without changing its velocity or direction of liquid droplets. Velocity difference between phases is called "slip" and the ratio of phase velocities is called the "slip ratio". In ideal mixing, homogeneous flow, the slip ratio is unity. This is an extremely rare flow pattern in actual hydrocarbon production flows and it only exists at extremely high pressure and flow rates. Therefore in most real world applications, both the gas phase velocity and the liquid phase velocity must be known, and if they are not the same, the slip ratio must be accounted for with correlations based on "slip models".

To accomplish this particular technique, the supply gas velocity must be known, 1) the gas velocity at the probe entrance must be maintained equal to the supply gas velocity, and 2) the probe entry design must be shaped such as not to disturb the flow pattern of the liquid droplets. This approach, even under closely controlled conditions, is not accurate enough for custody transfer measurement. Therefore, it is neither a good nor a practical method for sampling wet gas on an "ongoing" basis.

The liquid phase dispersion is dependent on the balance of forces acting upon it. The liquid in a horizontal wet gas flow is driven downstream by the gas flow. As the line pressure and/or the gas flow rate increase the energy available to drive the liquid increases. Therefore, the entrained liquid dispersion in a wet gas sample could be an ever changing dynamic condition. There are several forms of liquid which may be present in the transport line other than suspended liquid droplets, such as annular films, slugs, plugs, bubbles, mist, stratified regions, etc. Therefore unless the sample is perfectly mixed or homogenized, measurement of only the suspended droplets entering the opening of prior art probes (tube or pipe openings) is not an indication of the total gas and liquid present in the transport line.

There is a company named Petrotech as of Kvala, Norway (hereinafter PETROTECH) which utilizes an isokinetic Natural gas technique called ISOSPLIT®. The method consists of static mixing the two phases followed by dynamic isokinetic sampling of the resulting mixture. As previously stated this technique is difficult to execute and produces less than desirable results. It is primarily employed at the well head. The PETROTECH U.S. Pat. No. 5,538,344 relates primarily to the positioning of a mixing body within a pipeline.

Another reason for requiring accuracy in the sampling of wet natural gas is that reservoir simulation models are based on compositional analysis, and gas allocations are also made on that basis.

With the dynamic isokinetic sampling technique, sample gas flows continuously during the sampling process.

In conclusion, the above isokinetic sampling systems are designed to insure an isokinetic fluid flow of process gas into the opening of a probe and therethrough to an external location. With such a configuration, the fluid stream velocity must be known and the fluid velocity entering the probe must be controlled, which makes the technique generally impractical for typical field sampling of fluids.

GENERAL SUMMARY DISCUSSION OF THE INVENTION

Unlike the above discussed, prior art dynamic isokinetic sampling systems, the present invention teaches a new and innovative "integral slice" sampling process, wherein a very thin slice of the total volume of the source fluid flowing through a conduit or pipeline is captured by a streamlined container arrangement suspended in said source fluid, in a similar manner to an integral in calculus—a limiting procedure which approximates the area of a curvilinear region by breaking the region into thin vertical slices—with nominal flow disturbance, and in which trapped fluid is subsequently withdrawn and isolated in a location outside of the source fluid flowing stream.

Unlike the dynamic isokinetic techniques, the system of the present invention insures that the representative sample taken either in spot, batch or continuous fashion is not allowed to disassociate due to the very small internal cavity. The pipeline area is very large compared to the probe's very small interior and because of this vast difference; fluid in the probe will always be of a higher velocity than the pipeline fluid.

The high gas velocity (higher than the source velocity of the pipeline) of the very small internal cavity would then sweep all of the liquid particles at the same velocity as the gas particles being transported from the source to the probe. Therefore it would remain "associated" with the gas from which it condensed. High velocity gas in the small internal diameter bore of the probe will prevent any significant layer of liquid from accumulating on the surfaces. Even if an ultra-thin layer were to coat the probe's interior, the total area is so small that the impact would be negligible.

The present invention provides a far superior sampling solution for wet gas streams, including high HC dew point gases, which traditionally have been difficult to sample dynamically due to phase changes and resulting composition changes which can be triggered by flow, pressure, and/or temperature.

BRIEF DESCRIPTION OF DRAWINGS

For a further understanding of the nature and objects of the present invention, reference should be had to the following detailed description, taken in conjunction with the accompanying drawings, in which like parts are given like reference numerals, and wherein:

FIG. 1 is a side, perspective frontal view of the slotted probe tip of the preferred, first embodiment of the present invention, which is particularly suitable for use in continuous mode sampling, such as with on-line analyzers and the like.

FIG. 2 is a side, perspective view of the embodiment of the slotted probe tip of FIG. 1, illustrating the probe lowered into a pipeline containing a process gas stream containing entrained liquid or the like.

FIG. 3A is a frontal view of an alternative embodiment of the slotted probe tip of FIG. 1, wherein there has been added helical strakes added to the outer surface to diminish vibration caused by resonance effects associated with high velocity fluid probes engaging probes and the like.

FIG. 4A is a frontal view of the second embodiment of the Invention, illustrating a slotted probe suitable for use in batch mode sampling/analysis for on-line analyzers or the like.

FIG. 4B is a side view of the embodiment of FIG. 4A.

FIG. 4C is a bottom, end view of the embodiment of FIG. 4A.

FIG. 4D is a top, end view of the embodiment of FIG. 4A

DETAILED DISCUSSION OF THE INVENTION

First Embodiment of the Invention—Continuous Sampling for On-Line Analyzers

Figure 1:
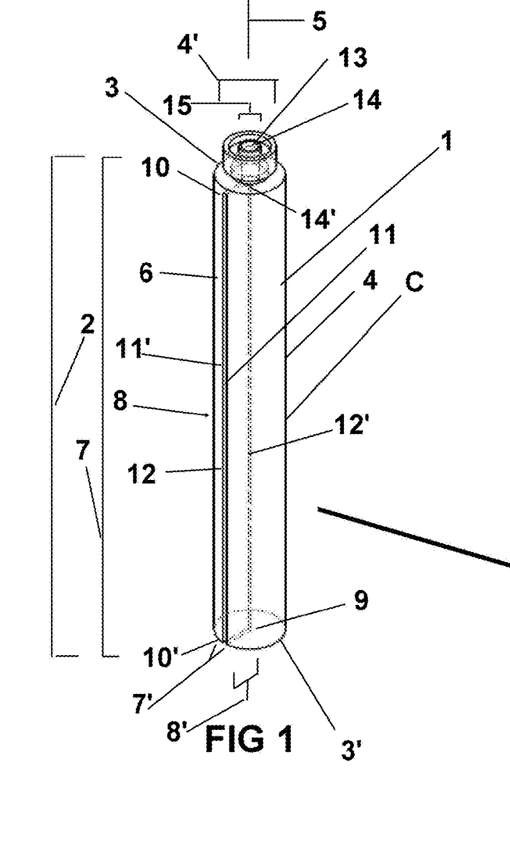
Figure 2:
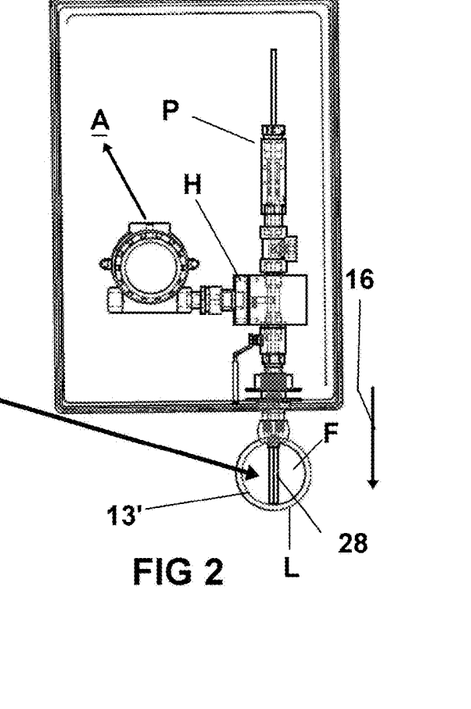
Figure 3A:
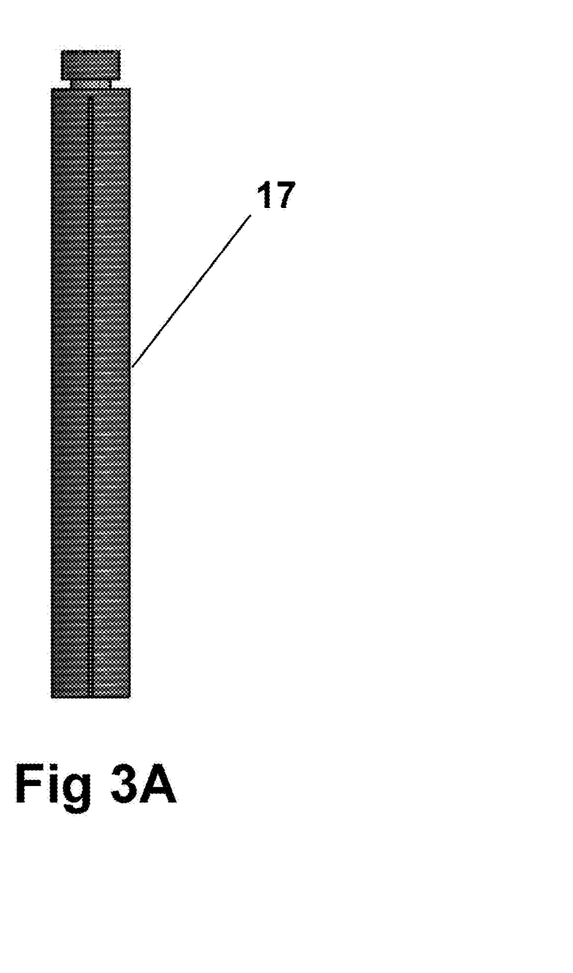
Figure 3B:
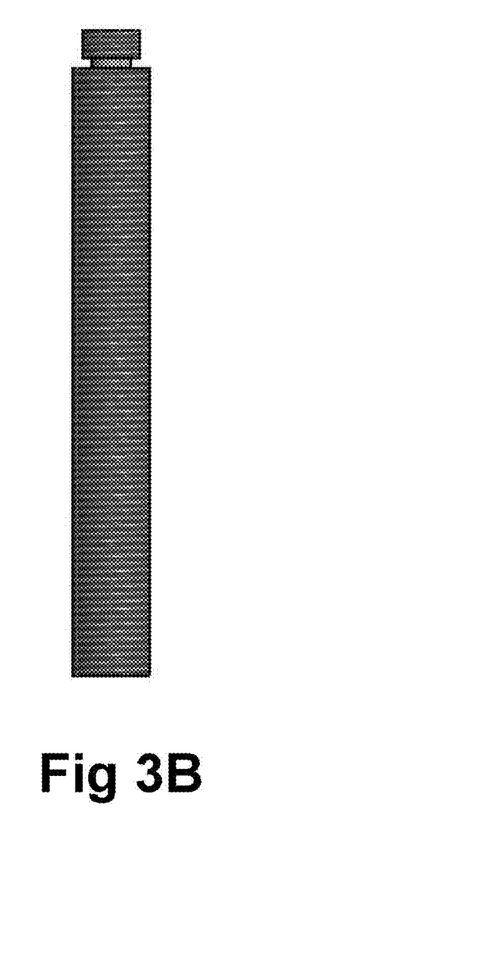
FIG. 3B is a rear view of the embodiment of FIG. 3A.
Figure 3C:
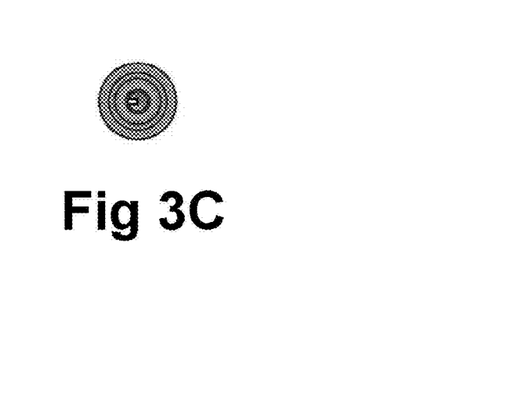
FIG. 3C is a top, end view of the embodiment of FIG. 3A.
Figure 3D:
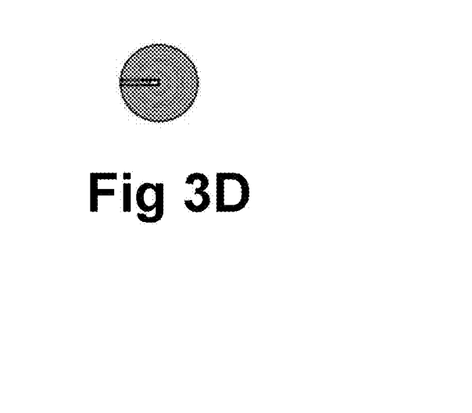
FIG. 3D is a bottom, end view of the embodiment of FIG. 3A.

Referencing FIGS. 1-2, the device of the present invention contemplates a sample collection apparatus for use collecting a fluid sample from a fluid stream F in a pipeline L or the like. In the preferred embodiment of the present invention, the apparatus is in the form of a sample collection container C or housing which may be mounted to an insertion probe P or the like to form a slotted probe tip 28 or the like comprising a body 1 having a length 2 forming a longitudinal axis 5 and terminating in first 3 and second 3' ends. As the body 1 in the present embodiment shown is in the form of a cylinder (although this may vary with application), the outer wall 4 forms an outer diameter 4' of the body.

Formed through the outer wall 4 of body 1 is an elongated, continuous or uninterrupted opening 6 having a length 7 aligned with the longitudinal axis 5 of the body 1, the opening 6 having a relatively narrow width 7', and ends 10, 10' to form a slot 8 penetrating the outer wall or surface of the body, the slot forming first 11 and second 11' side walls within the body having an outer edge 12 and an inner edge 12' corresponding to its depth 8' and outflow passage 13 having a small inside diameter as shown. In the preferred embodiment of the invention shown in the figures, the slot 8 preferably has a relatively uniform width corresponding to that of opening 6, while providing passage to the central axis 9 of the body 1 at the inner edge 12' of the slot, or about halfway through body 1. The slot as shown runs along the central axis 9 of the body 1, which corresponds to the longitudinal axis 5 of its cylindrical configuration forming the container C, although the length and position of the slot can vary depending upon the application.

As shown, the slot 8 runs from just below the first 3 end of body 1 to about the second end 3' of body 1, with the inner edge 12' of the slot 8 engaging outflow passage 13 having a small inside diameter, as shown, at the first, upper end 3 of body 1, said first end 14 of outflow passage 13 having a small inside diameter, as shown, which is formed to engage, as required, probe P to provide a flow of fluid therefrom, the outflow passage 13 in the present embodiment preferably having a diameter 15 no larger than the width 7' of elongated opening 6 forming the slot.

The present system is formed to collect via the slot in the slotted probe tip a "linear sample" spanning the diameter of the pipe, from side-wall to side-wall, or in this case from top to bottom, providing a representative sample of fluid the fluid stream wherein a fluid sample of the fluid stream is collected along a line spanning the inner diameter of said pipe, even where there is present entrained liquid particles and even flowing liquid droplets/streams along the lower and/or upper surfaces of the pipe. While the present figures illustrate the position of the probe tip as vertical, this is not intended to be limiting, as the probe can be oriented at any angle relative the pipe, as long as the probe interface (insertion point) allows it.

The slot and outflow passage are preferably relatively narrow (less than 1/32" depending on the volume of fluid being sample, the speed, viscosity, and other factors) to remove a very thin slice of the total breadth of the fluid stream, so as to provide an accurate composite of the total fluid flow using principals similar to the integral principle as used in calculus.

As described, the body forming the container has a first and second ends defining a length therebetween, with a slot defining a narrow opening to a centrally disposed outflow passage of preferably equal or less internal diameter than the slot width, said outflow passage preferably of equal or less area than the slot area, thus providing the "integral slice" (in the present example, less than 1/32" wide slot from the outer surface of the probe) to intersect the small ID outflow passage (less than 1/32"), so that process fluid having sample gas containing entrained liquid therein passes into the slot then is urged through the outflow passage to the probe at an equal or higher velocity than the fluid stream, so as to preserve the composition of the fluid stream and prevent disassociation of same.

It is emphasized that the "linear sample" forming the integral is preferably taken at a length corresponding to the maximum diameter of the process pipeline. In the embodiment illustrated in FIG. 2, the sample, once taken, is then directed into a heated zone H to vaporize any liquids, providing a single phase sample, then to a process analyzer, monitor, sample container, or other end use.

The system of the present invention insures that the representative sample taken either in spot, batch or continuous fashion is not allowed to disassociate by providing the very small internal cavity forming the outflow passage, to maintain or enhance the fluid flow velocity through the system. The pipeline area is very large compared to the probe's very small interior and because of this vast difference, fluid in the outflow passage from the slotted probe tip to the probe will always be of a higher velocity than the pipeline fluid.

The high gas velocity (higher than the source velocity of the pipeline) of the very small internal cavity/fluid outflow passage is formed to sweep all of the liquid particles at the same velocity as the gas particles being transported from the source to the probe. Therefore it would remain "associated" with the gas from which it condensed. High velocity gas in the small internal diameter bore forming outflow passage engaging the relatively narrow slot of the probe will prevent any significant layer of liquid from accumulating on the surfaces. Even if an ultra-thin layer were to coat the probe's interior, the total area is anticipated to be small that the impact would be expected to be negligible.

Continuing with the figures, as shown, the slotted probe tip 28 of the present invention is engaged to the end of an insertion probe P then is lowered into a pipeline L until the second, lower end 3' of the body 1 engages the opposing inner sidewall (in this case, the bottom) of the pipe containing a process gas stream F containing entrained liquid, with the opening 6 forming the entrance of the slot 8 facing the flow stream.

A portion of the fluid stream comprising a "linear slice" comprising the diameter of the pipe then passes into the opening, into and through the slot, then through the pressure of the flow stream is urged through the outflow passage for heating and/or collection, online analysis, monitoring, or other usage. As earlier indicated outflow passage in the preferred embodiment has an inner diameter commensurate with the width of the slot formed in the body forming the slotted probe tip, resulting lesser area than the slot, so as to facilitate at least equal but more likely greater fluid velocity flow through said outflow passage, to keep the fluid from slowing and possibly disassociating.

Referring to FIGS. 3A-3D an added feature of the slotted probe tip of FIG. 1 is shown, wherein helical strakes 17 have been added to the entire outer wall 4 of body 1 forming the slotted probe tip of the present invention, the helical strakes formed to diminish vibration caused by resonance effects associated with high velocity fluid probes flowing by the probe tip in operation.

Figure 10:
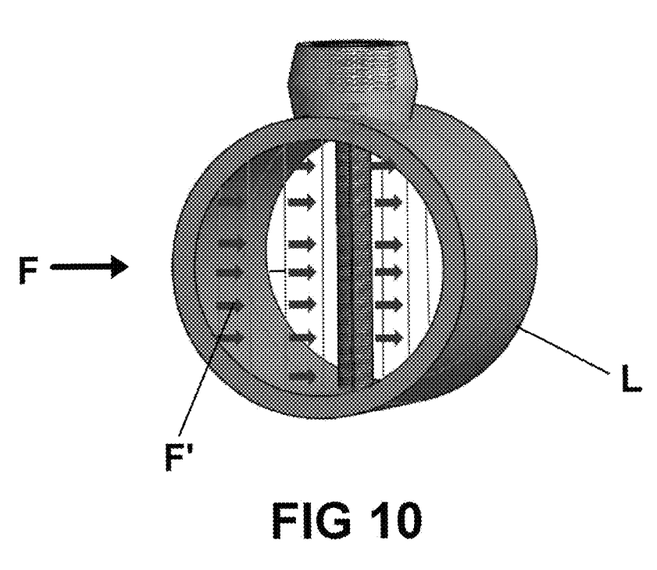
FIG. 10 is a perspective view of the slotted probe tip of FIG. 3A positioned laterally into a pipe so as to so as to engage the flow of a fluid stream substantially transversally, further illustrating fluid flow into the slot formed in said body to said fluid passage formed therein so as to provide a fluid sample collected from a sample area, in this view, the sample comprising a span associated with the diameter of said pipe.
Figure 11:
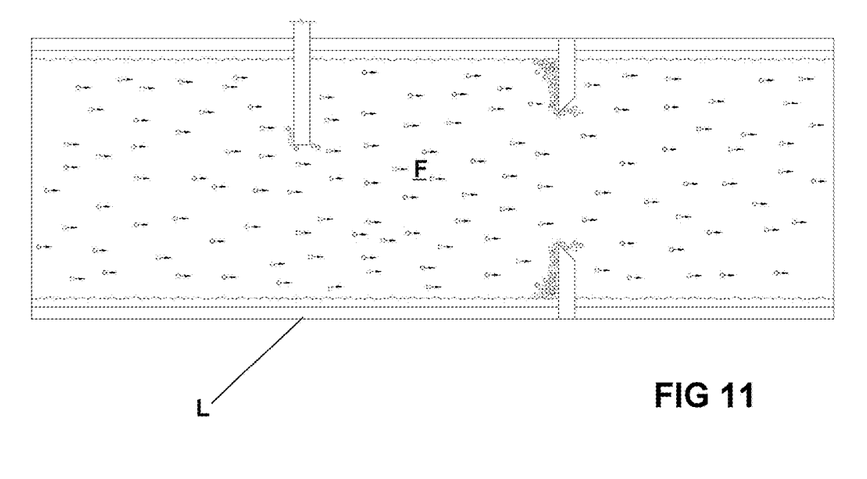
FIG. 11 is a cut-away view of a length of pipe having a process gas stream flowing therethrough, the gas stream comprising gas, entrained liquid particles, and liquids flowing along the inner wall of the pipe.

FIG. 10 illustrates the straight flow path of a "lateral slice" taken by the slotted probe tip of the present invention, wherein the flow through a pipeline or the like is taken, which, unlike the conventional spot sampling probes, in a manner which spans the entire internal diameter along a line from top to bottom of the ID of the pipe, and substantially along the entire length of the slotted probe tip, and ideally encompassing all strata (see FIG. 10, for example) present in the fluid flow.

Continuing with the Figures, the second, lower end 3' of the body 1 forming the slotted probe tip preferably engages the bottom of the pipeline so that fluids flowing therealong are collected via the sample slot along with aerosols and gas comprising the flow stream, so as to provide the most accurate "slice" of the flow through the pipeline. Also, the slot in the preferred embodiment, while sampling, would be positioned directly facing the fluid flow stream, so as to receive the sample without the sample having to divert through a containment area into the outflow passage, the sample flowing straight through the slot into the body (and outflow passage as desired, or contained within the body), with flow on opposing sides of the slot engaging the body being diverted about the outer wall of the probe via the radial surface of the probe.

Figures 4A, 4B, 4C, 4D:
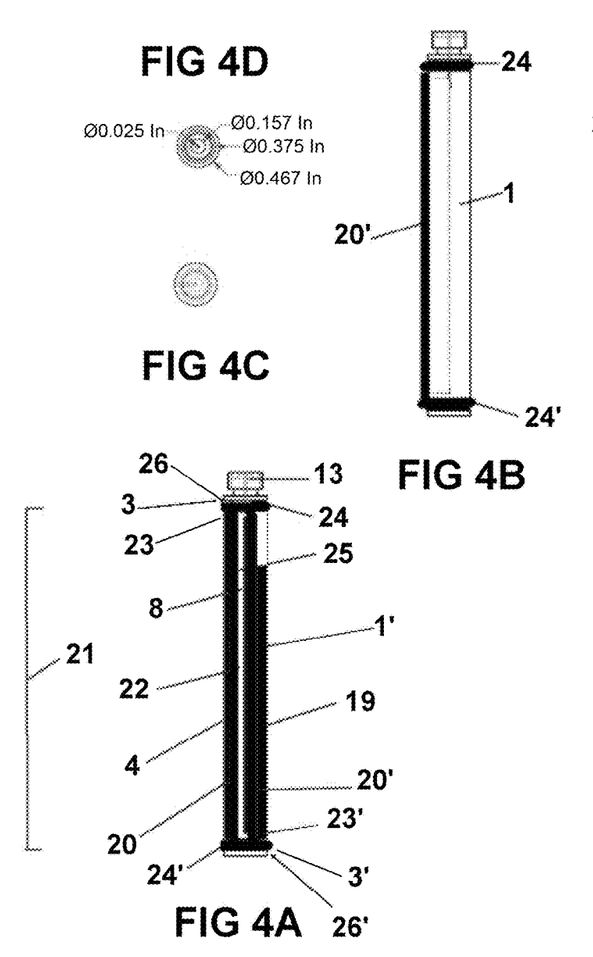
Figure 5:
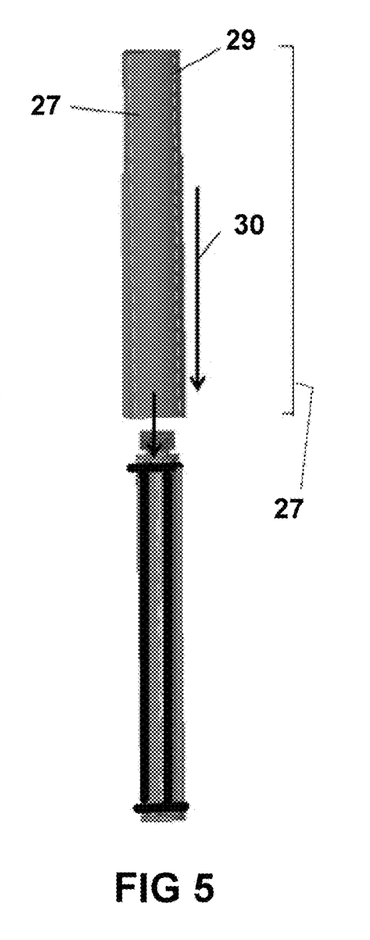
FIG. 5 is as frontal view of an embodiment of FIG. 4A, further illustrating a cover/closure for batch or spot mode operation that is formed to lower over the exposed probe, engaging seals therebetween so as to contain fluids in said slotted probe and cease flow of fluid from the fluid stream into the slotted probe tip.

FIGS. 4A-C illustrate a second, alternative embodiment of the present invention having the same components/general configuration of the slotted probe tip of FIG. 1, but added features particularly suitable for batch mode for continuous sampling for on-line analyzers or the like showing a cover/closure used to seal off the fluid contained therein, so the slotted probe tip can be retrieved via the insertion probe into the housing for heating in a heated zone then transported for batch analysis, as will be described herein.

As shown, the body 1' forming the slotted probe tip of the present invention has the same slot 8 configuration as that described in FIG. 4A and may include a outflow passage 13 (which may or may not be valved), but with the added feature of first 20 and second 20' longitudinal seals having first 23 and second ends 23' mounted to the outer wall 4, said first 20 and second 20' longitudinal seals being spaced 22 lengthwise such that slot 8 is situated therebetween, providing a lengthwise elastomer seal, gasket or the like on both sides of slot 8, said seals 20, 20' preferably having a length at least equal to that of slot, and in the present embodiment said seals 20, 20' have length substantially that of body 1'.

Also provided in this second alternative embodiment, in communication with the first 23 and 23' ends of said seals 20, 20', is first 24 and second 24' ring seals, respectively, said ring seals 23, 23' mounted at opposing ends 3, 3' of body 1', respectively, and engage the ends of said seals 20, 20' to form a containment area 25 between the longitudinal seals 20, 20' and said ring seals 24, 24', to selectively contain slot 8, as will be further explained infra. In the present embodiment, said seals or gaskets may be formed of an elastomer, and the ring seals 24, 24' may comprise o-rings, for example, and are mounted on grooves 26, 26' respectively, the above providing a sealable probe tip 19.

Referring to FIGS. 5, 7A-B and 8, a cover 27 may be used having an inner diameter 29 to envelop the body 1' along its length from first 24 to second 24' ring seals, the inner diameter 29 of cover 27 formed to engage seals 20, 20', 24, 24' to enclose and fluidly seal containment area 25 as said cover is positioned over same, providing a slotted probe tip with cover/closure for batch or spot mode operation. As shown, the cover may be lowered over the probe after it has already been exposed to the fluid flow in the pipeline L, so as to cease the flow of fluids therein.

Figure 6A:
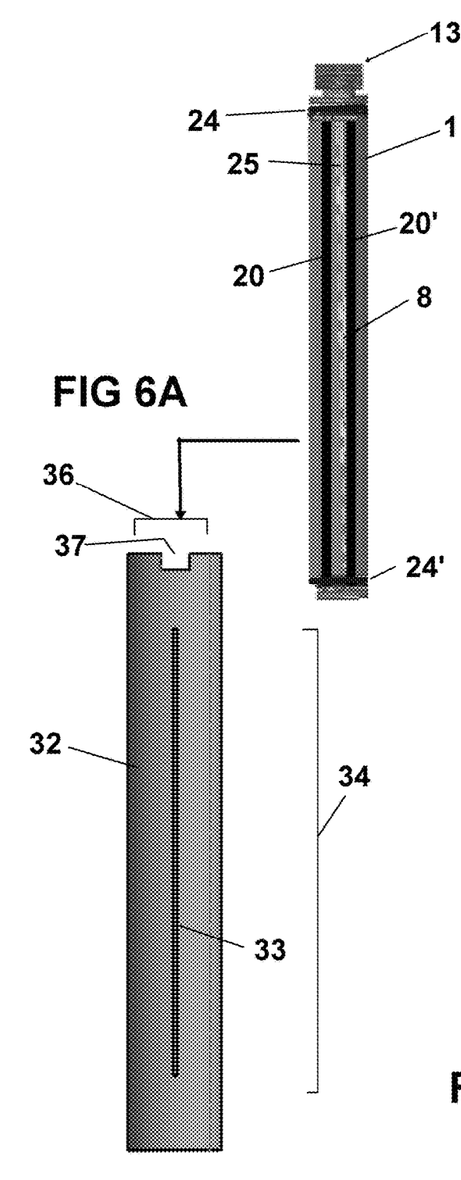
FIG. 6A is a frontal view of the slotted probe tip of FIG. 4A, illustrating another embodiment wherein there is provided a cover having a longitudinal slot formed therethrough from its first to second ends for batch or spot mode operation, said cover with slot formed to envelop said probe, said cover being rotatable so as to selectively regulate the flow of fluid into said probe via said slit.
Figure 6B:
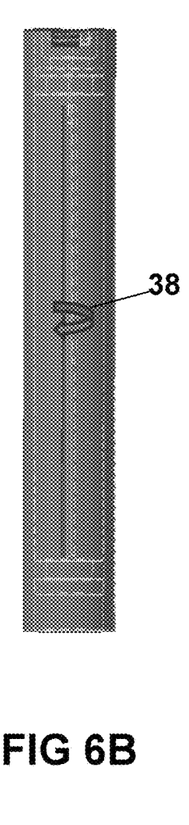
FIG. 6B illustrates a frontal view of the invention of FIG. 6A, wherein the cover/closure is shown in non-aligned, "blocked" or closed position.
Figure 6C:
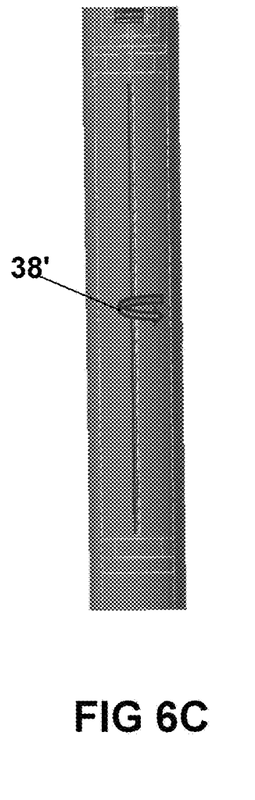
FIG. 6C illustrates a frontal view of the invention of FIG. 6A, wherein the cover/closure is shown in aligned, open position.
Figure 7A:
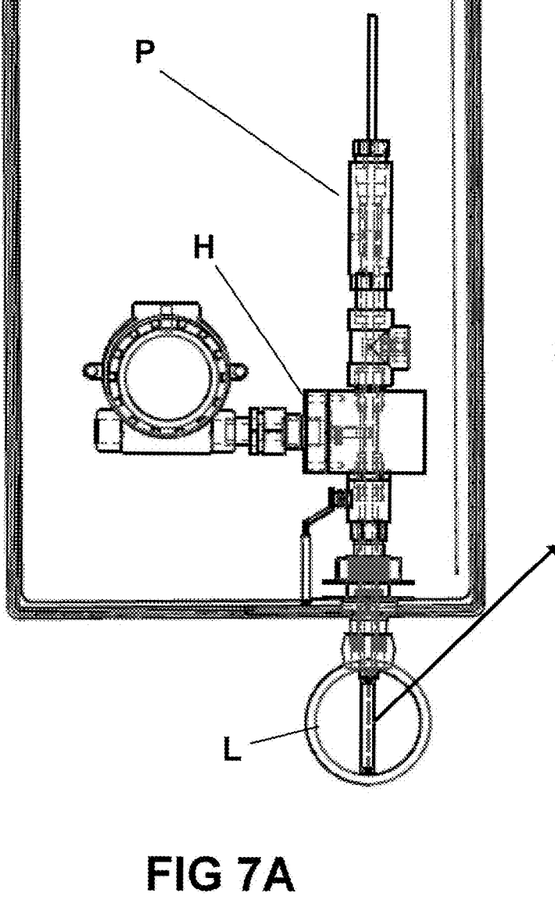
FIG. 7A illustrates a front view of the embodiment of FIG. 5 mounted to a probe tip in a pipe.
Figure 7B:
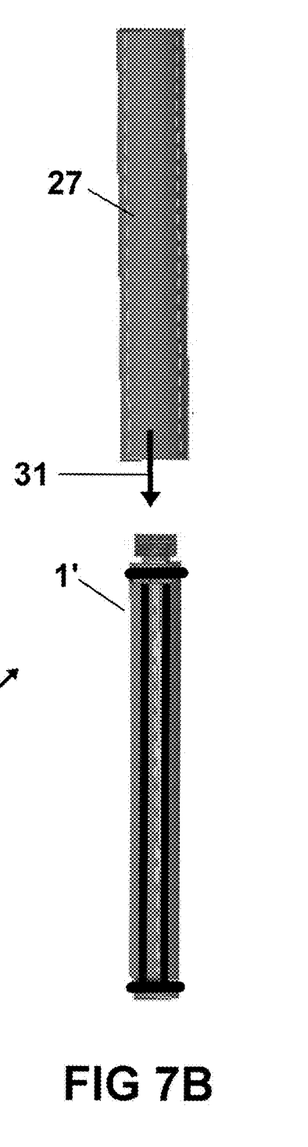
FIG. 7B illustrates the probe Tip of FIG. 7A illustrating the cover positioned to envelop same.
Figure 8:
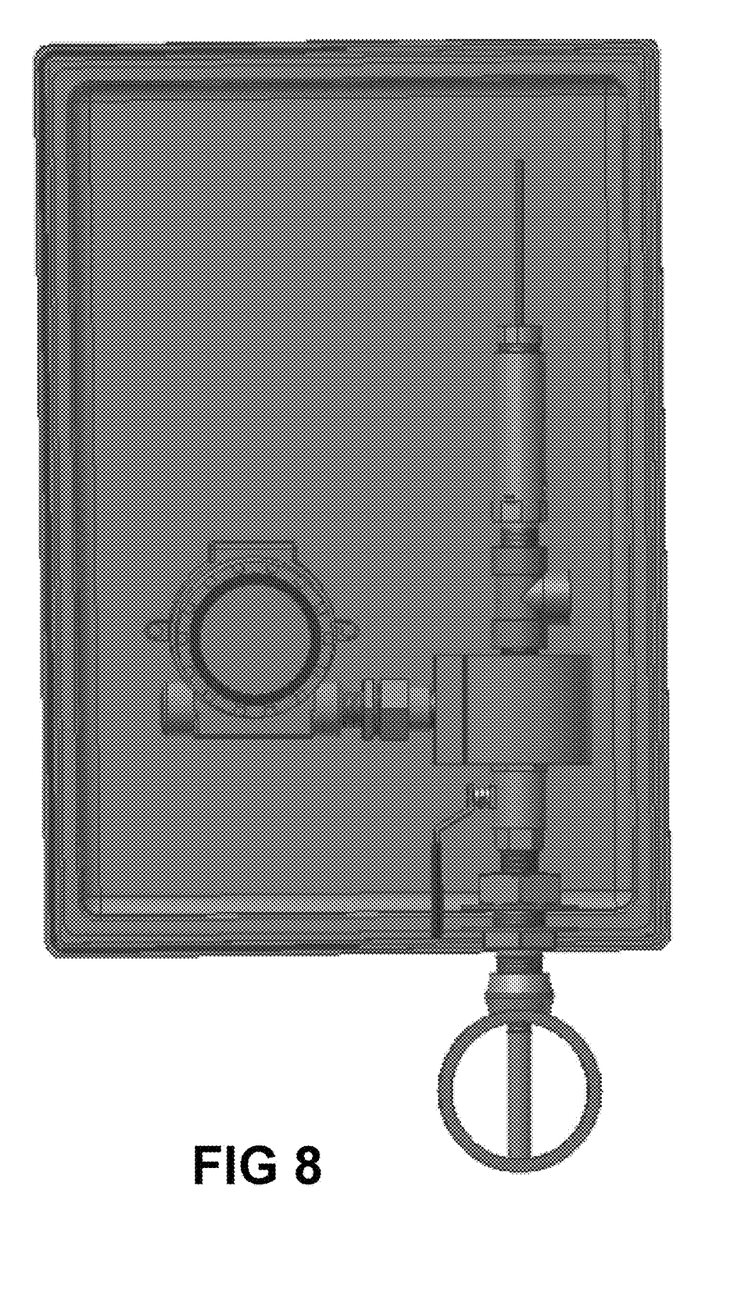
FIG. 8 is a frontal view of the third embodiment of FIG. 7A illustrating the cover/closure enveloping the slotted probe tip to seal off fluid contained therein, providing sealed container, allowing said sealed container to be retrieved via said probe into the housing where it may be heated prior to analysis.

FIG. 6A-6C illustrates the slotted probe tip of FIG. 4A, for use in batch or spot mode operation wherein the cover is in place over the probe tip while it is exposed to the process fluid.

As shown, the cover 32 is provided having a slot 33 formed through the cover between its first and second ends, said cover formed to envelop said slotted probe tip such that the inner diameter 36 of cover then engage the end 24, 24' and side longitudinal seals 20, 20' of said probe forming containment area 25 between the seals and about the probe slot 8, the cover having a cut-out 37 to facilitate a degree of rotation 38' of the cover along its longitudinal axis while enveloping the cover, so as to selectively align the slot 33 of the cover with the slot 8 of the probe tip while placing the slot 4 over the containment area 25 of probe, thus facilitating the flow of fluid from the fluid stream (FIG. 6C) through cover slot 33 into probe slot 8 for collection of a batch sample, then the cover is rotated 38 (FIG. 6B) so that the slot in the cover is no longer aligned with the slot of the probe, ceasing flow of fluid therein, wherein the slot 33 is positioned outside of the containment area 25 of the probe, or blocked due to engagement with the longitudinal seal (20 or 20').

As shown in FIG. 6B, the cover is blocked in this example by rotating the cover counterclockwise, putting the slot of the cover out of alignment with the slot of the slotted probe tip and out of the containment area 25, resulting in passage of fluid from the fluid stream to the slot 8 formed in said probe tip being blocked, and any fluid sample in the body 1 being contained, at which point the unit with the sample can be withdrawn from the pipe via the probe, heated via heated zone H to reduce any fluids in the sample to a gaseous state (if desired), then conveyed for batch analysis, monitoring, or the like.

Conversely, referring to FIG. 6C, in the present example, rotation 38' clockwise of the cover to align the cover slot 33 with the probe slot 8 effectively opening same to allow passage of fluids therethrough.

The use of "clockwise" and "counter-clockwise" in the above discussion was for exemplary purposes only and was not intended to be limiting, as either direction could be used to align the slots in the present system.

Third Embodiment of the Invention—Spot Sampling for Off-Site Lab Analysis

Figure 9A:
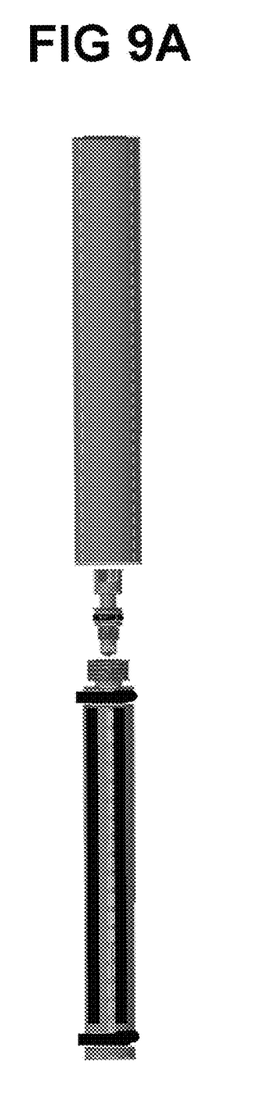
FIG. 9A is a side view of a third embodiment of the present invention, suitable for spot sampling, illustrating an embodiment of the slotted probe tip having a valve at one end, upper and lower seals and opposing sealing gaskets on either side of the slot formed in the probe tip formed to engage the cover for selectively sealing same to contain a sample collected therein.
Figure 9B:
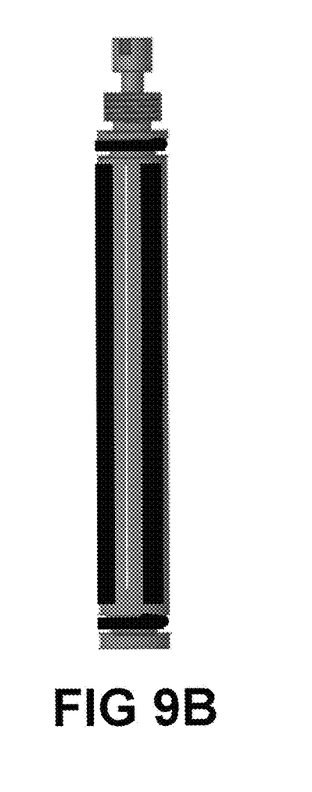
FIG. 9B is a side view of the slotted probe tip of FIG. 9a illustrating the valve mounted to the first end of the unit.
Figure 9C:
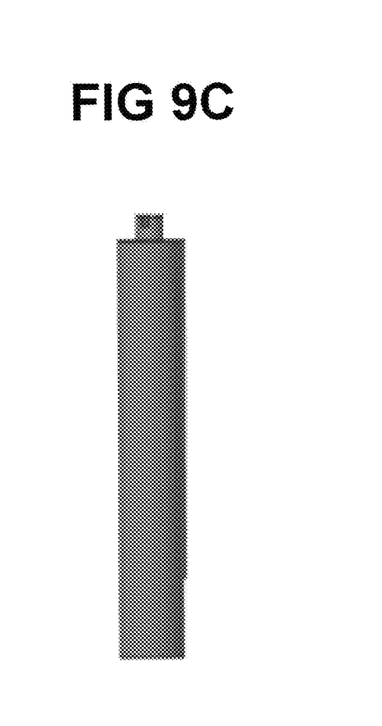
FIG. 9C is a side view of the slotted probe tip with cover of FIG. 9A, with the cover enveloping and sealing outer wall of the unit, and the valve mounted to the end thereof.

FIGS. 9A-9C illustrate a fourth embodiment of the invention, wherein the slotted probe tip of FIG. 4A is used in a spot sample mode, providing in effect a sample cylinder. As shown, A valve is added to the batch mode embodiment so that the probe tip can now be removed after having been exposed to the fluid stream, the cover lowered so as to enclose same, the unit retracted sent to a lab for analysis. As with other sample cylinders, it is noted that this embodiment may be evacuated prior to use or not, purged or not, evacuated and purged or not.
Options
Heated zone or not
Heated enclosure or not
Regulator or not
Heated regulator or not
Multistage regulator or not
A heated multistage regulator may be incorporated into the probe or not
Mayeaux J T regulator U.S. Pat. No. 8,220,479 (incorporated herein by reference thereto) may be used as desired.
Heated Mayeaux J T regulator U.S. Pat. No. 8,220,479 (incorporated herein by reference thereto) may be used as desired.
The heated components may be powered of f the existing heat trace.

RECITATION OF ELEMENTS

H Heated Zone
F, F' fluid stream Flow
L pipeline
P insertion probe
C container
1 body
2 length
3, 3' first upper, second lower ends
4, 4' outer wall, outer diameter
5 longitudinal axis
6 Elongated opening (continuous)
7, 7' length, width
8' depth
8 slot
9 central axis
10, 10' first and second ends and
11, 11' first and second side walls having
12, 12' outer, inner edge
13 outflow passage
13' ID pipe
14' outflow passage ends
15 outflow passage diameter
16 lowered
17 helical strakes
18
19 Second embodiment of slotted probe tip with seals
20,' first, second opposing longitudinal seals
21 length
22 space therebetween
23, 23' ends
24, 24' first, second ring seals
25 containment area
26,' groove
27 length
28 slotted probe tip
29 inner diameter
30 slide to envelop
31 lowered
32 cover
33 slot
34 length
35 envelop
36 ID
37 cut-out
38 rotation The present invention may be used in places where in addition to expected desirable components, there may be found undesirable injected components such as glycols and scavengers. However, it is believed that a combination of phase diagram data and empirical testing could lead to a guide for the slot geometry for the particular pipeline application the invention would be used in.

The invention embodiments herein described are done so in detail for exemplary purposes only, and may be subject to many different variations in design, structure, application and operation methodology. Thus, the detailed disclosures therein should be interpreted in an illustrative, exemplary manner, and not in a limited sense.

I claim:

1. A device for sampling fluid comprising gas with entrained liquid in a fluid stream in a pipe having an inner wall forming an inner diameter, comprising:
    a body having first and second ends and a length,
    a fluid passage provided at said first end of said body;
    said body having a slot having a cross sectional area, said slot in longitudinal alignment with said body, said slot forming a conduit to facilitate the flow of fluid from said fluid stream to said fluid passage at least at the velocity of said fluid stream;
    said fluid passage having a cross sectional area sized in relation to the cross sectional area of said slot so as to facilitate the flow of fluids therethrough at least at the flow velocity of fluid flowing through said slot;
    whereby, after laterally positioning said device into a pipe so as to engage the flow of the fluid stream substantially transversally, a portion of said fluid stream flows into said slot formed in said body, through said slot then through said fluid passage at least at the velocity of said fluid stream, so as to prevent disassociation of the entrained liquid from the gas, and provide a representative sample of said fluid stream.

2. The device of claim 1, wherein said fluid passage formed in said body has a cross-sectional area less than the cross sectional area of said slot so as to facilitate the flow of fluid therethrough at a higher velocity than fluid flowing through said slot.

3. The device of claim 2, wherein said first end of said body comprises a threaded connection.

4. The device of claim 3, wherein said first end of said body further comprises a valve to selectively control fluid through said conduit.

5. The device of claim 4, wherein said first end of said body engages an insertion probe, to form a sample probe tip therefore.

6. The device of claim 5, wherein said sample probe tip is formed for fluid sample collection.

7. The device of claim 4, wherein said conduit is formed to convey said representative sample to a heated zone.

8. The device of claim 3, wherein there is further provided a valve to close said conduit, so as to provide a sample container.

9. The device of claim 2, wherein said slot is sized and positioned to facilitate a proportionate collection of fluids flowing through said pipe at a predetermined area of said fluid stream.

10. The device of claim 9, wherein said slot is sized and positioned to facilitate a proportionate collection of fluids flowing through said pipe at a medial area of said fluid stream.

11. The device of claim 2, wherein said slot is formed to collect a linear flow of said fluid stream substantially across the internal diameter of said pipe, so as to provide a representative sample thereof.

12. The device of claim 2, wherein said slot formed in said body as a width and said fluid passage has an internal diameter, said slot and said fluid passage each measuring less than 1/32".

13. The device of claim 1, wherein said slot formed in said body has a width, and said fluid passage has an internal diameter comparable to the width of said slot within a factor of 2.

14. The device of claim 1, wherein said device forms a sample probe tip, said body having first and second seals associated with said body, and wherein there is further provided an outer cover formed to envelop said body so as to selectively form a container to contain a sample therein.

15. The device of claim 14, wherein said outer cover is formed to slidingly engage said body along its length such that said outer cover engages said first and second seals to form a containment area therebetween.

16. The device of claim 1, wherein said body has an outer surface having helical strakes emanating therefrom.

17. The device of claim 16, wherein said helical strakes are formed to engage the fluid stream so as to diminish vibration due to interaction therefrom.

18. The device of claim 1, wherein said slot is straight and continuous.

19. The device of claim 1, wherein there is further provided a cover having an inner diameter, said cover formed to envelope said body to selectively prevent the flow of fluid through said slot.

20. The device of claim 19, wherein said body has first and second seals situated at said first and second ends of said body, respectively, formed to engage the inner diameter of said cover to provide fluid containment therebetween.

21. The device of claim 20, wherein said body further comprises first and second longitudinally aligned seals situated on opposing sides of said slot.

22. The device of claim 21, wherein said cover has formed therein a slot along its length, and wherein, upon slidingly engaging said cover to said body, said first and second longitudinally aligned seals, in conjunction with said first and second end seals form a containment area surrounding said slot formed in said body.

23. The device of claim 22, wherein said cover is formed to be rotatable along its longitudinal axis so as to selectively align the slot formed in said cover with the slot formed in said body, to selectively allow the passage of fluid therethrough.

24. The device of claim 1, wherein said slot has a width, and said fluid passage has an internal diameter equal to or less than said width of said slot.

* * * * *